(12) United States Patent
Upton et al.

(10) Patent No.: US 10,959,698 B2
(45) Date of Patent: Mar. 30, 2021

(54) IMAGE-BASED DIAGNOSTIC SYSTEMS

(71) Applicant: OXFORD UNIVERSITY INNOVATION LTD.

(72) Inventors: Ross Upton, Oxford (GB); Paul Leeson, Oxford (GB)

(73) Assignee: OXFORD UNIVERSITY INNOVATION LTD., Oxford (GB)

( * ) Notice: Subject to any disclaimer, the term of this patent is extended or adjusted under 35 U.S.C. 154(b) by 94 days.

(21) Appl. No.: 16/309,432

(22) PCT Filed: Jun. 13, 2017

(86) PCT No.: PCT/GB2017/051720
§ 371 (c)(1),
(2) Date: Dec. 12, 2018

(87) PCT Pub. No.: WO2017/216545
PCT Pub. Date: Dec. 21, 2017

(65) Prior Publication Data
US 2019/0247016 A1    Aug. 15, 2019

(30) Foreign Application Priority Data
Jun. 13, 2016   (GB) ...................................... 1610269

(51) Int. Cl.
*G06K 9/00* (2006.01)
*A61B 8/08* (2006.01)
(Continued)

(52) U.S. Cl.
CPC .......... *A61B 8/0883* (2013.01); *A61B 8/5223* (2013.01); *G06T 7/0012* (2013.01);
(Continued)

(58) Field of Classification Search
CPC ....... A61B 8/0883; A61B 8/5223; A61B 8/00; A61B 8/08; A61B 8/0891; A61B 8/485;
(Continued)

(56) References Cited

U.S. PATENT DOCUMENTS 6,728,394 B1 * 4/2004 Chen ....................... G06T 7/246
128/915
8,077,944 B2 12/2011 Schummers
(Continued)

FOREIGN PATENT DOCUMENTS

CA    WO2015168792 A9    11/2015
EP    1522875 A1    4/2005
(Continued)

OTHER PUBLICATIONS

GB Search Report from corresponding GB Patent Application No. GB1610269.1, dated Dec. 19, 2016, 5 pages.
(Continued)

*Primary Examiner* — Jose L Couso
(74) *Attorney, Agent, or Firm* — Lee & Hayes, P.C.

(57) ABSTRACT

A system for diagnosing a heart condition comprises an imaging system (102) arranged to acquire two images of the heart at respective points in the cardiac cycle, and locating means, which may be manually operated or automatic, for locating a series of pairs of points on the images. Each pair of points indicates the respective positions of a single part of the heart in the two images. The system further comprises a processor (108) arranged to calculate from the positions of said pairs of points a value of at least one parameter of the deformation of the heart. It may further be arranged to compare the value of the at least one parameter with reference data to generate a diagnostic output.

20 Claims, 5 Drawing Sheets

(51) Int. Cl.
*G06T 7/00* (2017.01)
*G16H 30/40* (2018.01)
*A61B 5/00* (2006.01)

(52) U.S. Cl.
CPC ... *A61B 5/0044* (2013.01); *G06T 2207/10132* (2013.01); *G06T 2207/30048* (2013.01); *G16H 30/40* (2018.01)

(58) Field of Classification Search
CPC ......... A61B 8/486; A61B 8/02; A61B 8/0866; A61B 8/4416; A61B 5/0044; A61B 5/055; A61B 5/02007; A61B 5/02028; A61B 5/1107; A61B 6/00; A61B 6/03; A61B 6/486; A61B 6/503; A61B 6/5217; A61B 6/032; A61B 6/5247; A61B 6/4417; A61B 6/507; A61B 2576/023; A61B 2576/00; A61B 2018/00351; G16H 30/40; G16H 50/30; G16H 50/20; G16H 50/50; G06T 2207/10132; G06T 2207/30048; G06T 2207/10016; G06T 2207/10076; G06T 2207/10081; G06T 2207/10088; G06T 2207/30101; G06T 2207/30104; G06T 7/0012; G06T 7/251; G06T 7/0016; G06T 7/20; G06T 7/149; G06T 7/38; G06T 7/215; G06T 2200/04; G06T 2210/41; G01R 33/32; G01R 33/5608; G01S 15/8981; G01S 15/8993; G01S 7/52036; G01S 7/52046; G01S 7/52063; G01S 7/52069; A61N 1/3627; A61N 1/368; A61N 1/3684; A61N 1/36842; G06K 9/6207; G06K 9/4604; G06K 9/48; G06K 9/6201; G06K 2209/05; G06K 2209/051; G06F 19/321; G06F 19/325; G01N 2291/02827; Y10S 128/922; A61M 5/1723
See application file for complete search history.

(56) References Cited

U.S. PATENT DOCUMENTS

| | | | |
|---|---|---|---|
| 10,765,407 B2* | 9/2020 | Yamagata | A61B 8/4494 |
| 10,776,998 B1* | 9/2020 | Wang | G01R 33/3607 |
| 2006/0074315 A1 | 4/2006 | Liang et al. | |
| 2007/0014452 A1* | 1/2007 | Suresh | G06T 17/20 382/128 |
| 2007/0299479 A1 | 12/2007 | Saksena | |
| 2008/0260230 A1* | 10/2008 | Gotardo | G06T 7/0012 382/131 |
| 2008/0262814 A1* | 10/2008 | Zheng | G06F 19/00 703/11 |
| 2008/0317316 A1* | 12/2008 | Ohuchi | G01S 7/52074 382/131 |
| 2009/0308745 A1 | 12/2009 | McLeod | |
| 2010/0074475 A1* | 3/2010 | Chouno | A61B 8/065 382/107 |
| 2010/0208957 A1* | 8/2010 | Chen | G06T 7/0016 382/128 |
| 2011/0035195 A1 | 2/2011 | Subbiah et al. | |
| 2011/0056876 A1 | 3/2011 | Takeshi et al. | |
| 2011/0243401 A1 | 10/2011 | Zabair et al. | |
| 2012/0089016 A1* | 4/2012 | Mizuno | G06T 7/20 600/425 |
| 2014/0334708 A1* | 11/2014 | Sakata | A61B 6/541 382/131 |
| 2015/0045662 A1* | 2/2015 | Kim | G06T 7/149 600/427 |
| 2015/0313510 A1* | 11/2015 | Razavi | A61B 5/0044 600/301 |
| 2017/0265843 A1* | 9/2017 | Abe | A61B 8/14 |
| 2017/0311839 A1* | 11/2017 | Osman | A61B 5/1107 |
| 2018/0014812 A1* | 1/2018 | Patil | A61B 8/543 |

FOREIGN PATENT DOCUMENTS

| | | |
|---|---|---|
| JP | 2005237555 A | 9/2005 |
| WO | WO2007054861 A2 | 5/2007 |

OTHER PUBLICATIONS

International Preliminary Report on Patentability from corresponding GB PCT Application No. PCT/GB2017/051720, dated Dec. 27, 2018, 20 pages.
International Search Report from corresponding GB PCT Application No. PCT/GB2017/051720, dated Aug. 14, 2017, 5 pages.
Steinhard et al., "OP18.11: Quantification of regional atrial contraction in the eftal heart using the parameters strain and velocity—a tissue Dopppler imaging (TDI) study," Ultrasound in Obstetrics Adn Gynecology, vol. 30, No. 4, Oct. 1, 2007, pp. 519-519, 1 page.
Written Opinion from corresponding GB PCT Application No. PCT/GB2017/051720, dated Aug. 14, 2017, 6 pages.

* cited by examiner

IMAGE-BASED DIAGNOSTIC SYSTEMS

CROSS REFERENCE TO RELATED PATENT APPLICATIONS

This Application claims priority to and is a national phase of PCT/GB2017/051720, filed Jun. 13, 2017, which claims priority to GB 1610269.1, filed Jun. 13, 2016, each of which are incorporated herein by reference in their entirety.

FIELD OF THE INVENTION

The present invention relates to systems for analysing medical images, for example of the heart, and for measuring parameters of the imaged subject. It has application in echocardiography, but also with other imaging modalities such as X-ray computer tomography (CT), magnetic resonance imaging (MRI), and positron emission tomography (PET).

BACKGROUND TO THE INVENTION

Echocardiography is widely used as a method of imaging the heart. It uses a series of rapidly acquired pulse-echo ultrasound images to build up, for example, a real time video image of the heart. The images are typically two dimensional (2D) and the images are typically analysed visually by a skilled clinician, although computer analysis of the images is known, for example from U.S. Pat. No. 8,077,944. In stress echocardiography, the heart is imaged in a rest condition, i.e. when the subject is at rest, and under a stress condition, for example after exercise. The function of the heart in the two conditions can be compared to provide information on how it responds to stress. If it is not appropriate for the subject to be exercised, then stress can be induced or simulated, for example by injecting a stimulant such as dobutamine into the subject. Dobutamine stress echo (DSE) is widely used in diagnosing coronary artery disease (CAD).

SUMMARY OF THE INVENTION

The present invention provides a system for measuring deformation of the heart, for example for diagnosing a heart condition, the system comprising an imaging system arranged to acquire two images of the heart at respective points in the cardiac cycle. The system may comprise locating means for locating a series of pairs of points on the images, each pair of points indicating the respective positions of a single part of the heart in the two images. The system may comprise processing means arranged to calculate, for example from the positions of said pairs of points, a value of at least one parameter of the deformation of the heart.

The processing means may be arranged to compare the value of at least one parameter with reference data to generate a diagnostic output.

The at least one parameter may include any one or more of: a displacement in at least one direction of a part of the heart; a mean, for all of said parts of the heart, of the displacements in at least one direction; the sum of displacements in two different directions, for example the longitudinal and radial directions, for at least one of said parts of the heart; the mean, for all of said parts of the heart, of that sum of displacements; and the principle transformation which is described in more detail below.

The locating means may comprise a user input device arranged to enable a user to locate said pairs of points in the images and to record the positions of said pairs of points, for example by recording the coordinates of each of the points in a two dimensional coordinate system.

The imaging system may be arranged to store the images as respective image data sets, and the locating means may be arranged to process the image data sets to determine the locations of said pairs of points and to record the positions of said pairs of points.

The at least one parameter may comprise a plurality of parameters and the processing means may be arranged to compare the value of each of the parameters with a respective reference value.

The system may be arranged to acquire a further set of two images of the heart at respective points in a cardiac cycle, with heart in a second condition, which is different from its condition when the first set of two images are acquired. For example one of the conditions may be a rest condition when the subject is at rest and one of the conditions may be a stress condition when the subject is under stress. Each of the parameters may be determined once for each set of images. One or more further parameters may be defined which combine data from the two sets of images. For example the difference in the value of one of the parameters, between the two sets of images, may be used as a further parameter.

The processing means may be arranged to define a decision tree for generating the diagnostic output from the values of the parameters. The decision tree may include a plurality of decision points. Each decision point may define a reference value of one of the parameters. For example one of the decision points may define a reference value of the principal transformation, and/or one of the decision points may define a value of the shear transformation as described in more detail below, and/or one of the decision points may define a reference value of the difference between the principal transformation in the two different conditions of the heart. Systems for building decision trees from training data are well known, such as C4.5 and J48.

The invention further provides a method of measuring deformation of the heart, for example for diagnosing a heart condition, the method comprising acquiring two images of the heart at respective points in the cardiac cycle, locating a series of pairs of points on the images, each pair of points indicating the respective positions of a single part of the heart in the two images. The method may further comprise calculating, for example from the positions of said pairs of points, at least one parameter of the deformation of the heart. The method may further comprise comparing the at least one parameter with reference data to generate a diagnostic output.

The invention further provides a method of producing a system for diagnosing a heart condition, the method including analysing a set of images, wherein each of the images has a diagnostic outcome associated with it, the method including calculating a value of the at least one parameter for each of the images, analysing the values and the diagnostic outcomes to determine a relationship or correlation between the two.

The method may further comprise using machine learning to develop a decision tree for generating the diagnostic output from the values of the parameters. The method may be performed on a computer system or processor system, which may form part of an imaging system, or may comprise a separate computer.

The diagnostic output may relate to a variety of cardiac conditions, such as coronary artery disease (CAD), or mitral regurgitation, or hypertrophic cardiomyopathy.

The imaging system may comprise an echocardiography system, or it may be an X-ray imaging system such as an X-ray computer tomography (CT) scanner, magnetic resonance imaging (MRI) scanner, or a positron emission tomography (PET) scanner.

The system or method may further comprise, in any workable combination, any one or more features or steps of the preferred embodiments of the invention, as will now be described with reference to the accompanying drawings.

DESCRIPTION OF THE PREFERRED EMBODIMENTS

Figure 1:
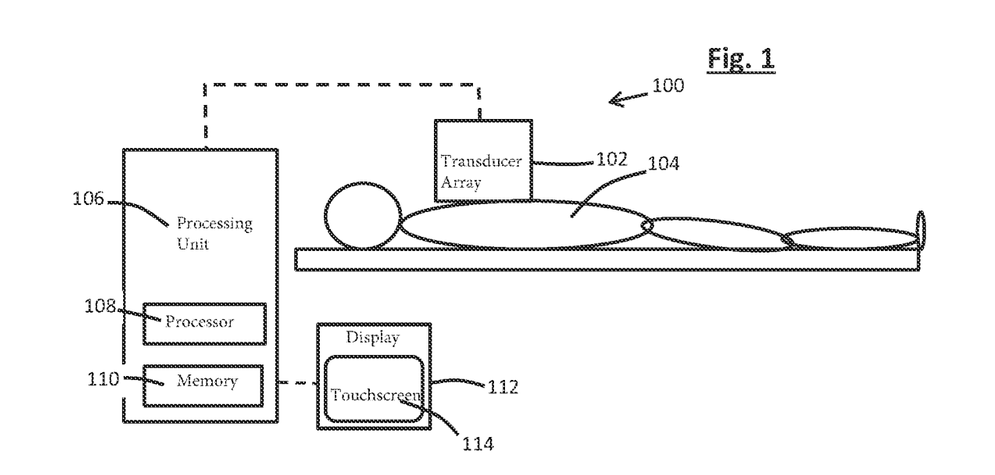
FIG. 1 is a schematic view of a system according to an embodiment of the invention.

Referring to FIG. 1, an echocardiography system 100 comprises a transducer array 102 arranged to be located close to the body of the patient 104, typically as close to the heart as possible, a processing unit 106 which includes a processor 108 which may be a digital electronic processor, a memory 110 such as a hard disk, and a display 112, such as a flat screen monitor or LED display. The system may further include a user input device, for example a touchscreen 114 integrated into the display 112, which provides a user input allowing a user to provide inputs to the system 100. Other user inputs such as a mouse, touchpad or keyboard may of course be used. The processor unit 106 is connected to the transducer array 102 and is arranged to control the transducer array as a phased array so as to emit an ultrasound beam which scans across the patient in a series of pulses, and detect reflected ultrasound from the heart from each pulse. One scan of the heart builds up a single image, and the scan is repeated at typically 25 to 50 images per second to build up a real time video image of the heart showing its movement during the cardiac cycle. Each image may be stored in the memory 110 as an image data set which may comprise, for example, intensity values for each of the pixels of which the image is made up.

While the system is described in general terms above, suitable echocardiography systems include, for example the Philips Epic iE33, GE vivid e9, or portable systems such as the Philips CX50, or hand held systems.

The process of echocardiography is well known and will not be described in detail. There are several different imaging methods, but two dimensional imaging may be used. It is known to provide images on several different planes through the heart, which show different aspects of the four main chambers of the heart, the left ventricle (LV), right ventricle (RV), left atrium (LA) and right atrium (RA). Such views include, for example, an apical four chamber view, apical two or three chamber views and parasternal long and short axis views. In each case, while a single still image can be obtained, typically a series of views is acquired over the cycle of the heart so that its movement can be recorded and analysed.

Figure 2:
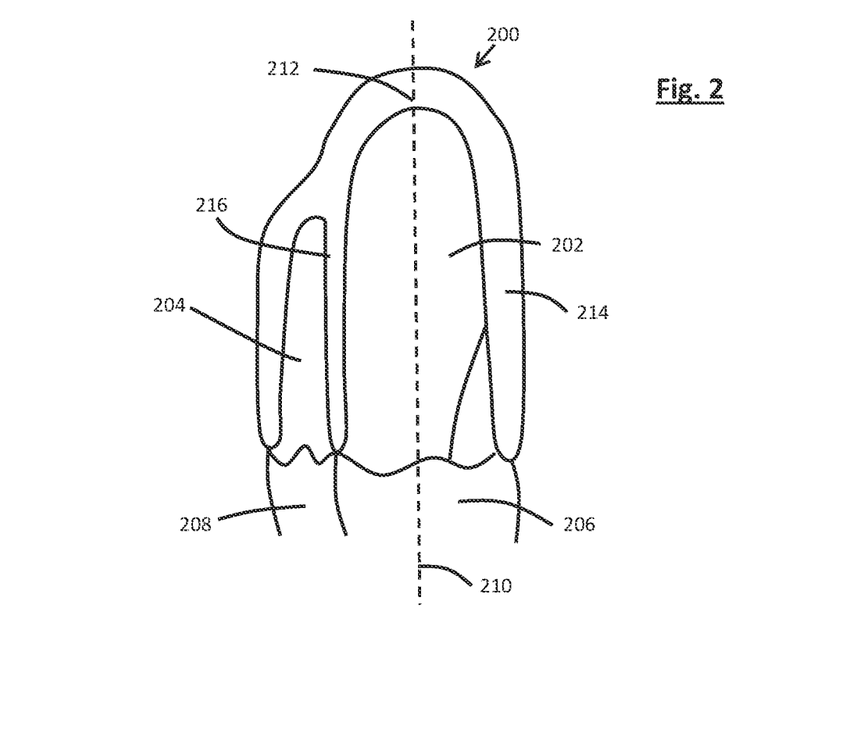
FIG. 2 shows schematically a four chamber view of a heart.

Referring to FIG. 2, if the images are four chamber apical views, they show a 2D plane of the heart 200 showing the left ventricle 202, the right ventricle 204, the left atrium 206 and the right atrium 208. The plane includes the long axis 210 of the LV, also extends through the apex 212 of the LV, the lateral wall 214 of the LV and the septum 216.

Figure 3:
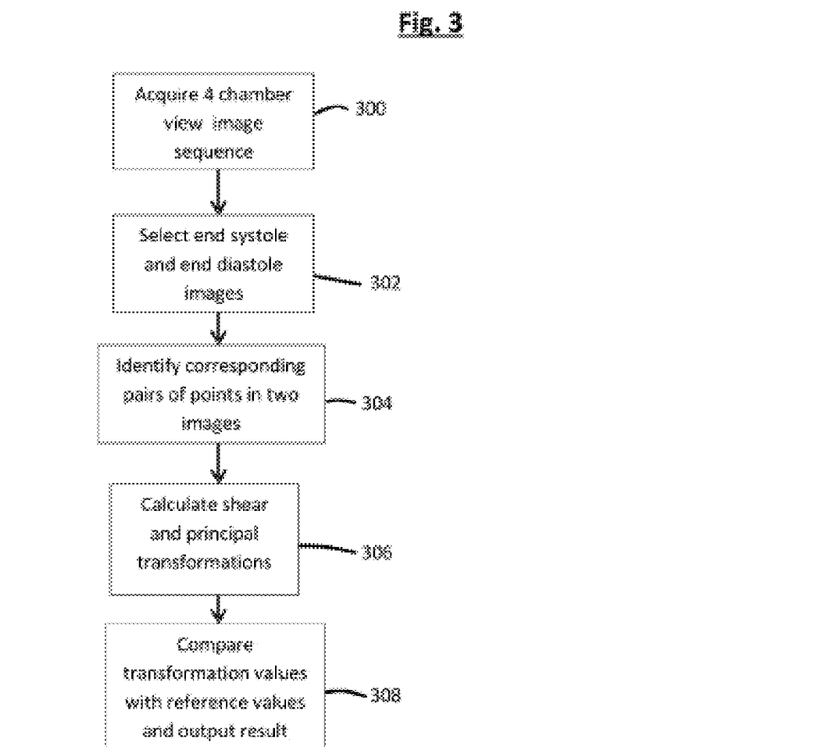
FIG. 3 is a flow diagram showing the main steps of a diagnostic method performed by the system of FIG. 1.

Referring to FIG. 3, the echocardiography system 100 may be arranged to acquire at step 300 a sequence of 2D images and store them in its memory 110. The images may be acquired over a single cardiac cycle, and may include for example between ten and 50 images covering one cycle. The acquisition of the images can of course be carried out on a conventional echocardiography system 100. The following analysis of the images can be carried out using the same processing unit 106 that forms part of the echocardiography system as shown in FIG. 1. However the images may be downloaded onto a computer, such as a laptop or PC, which has a processor, memory, user input and display, which operate for this purpose in the same way as those of the control unit 106, and the further analysis of the images may be carried out on that computer under the control of dedicated software.

At step 302, the images closest to end systole, i.e. maximum contraction, and end diastole, i.e. maximum volume of the LV, may be identified. This can be done by a user viewing all of the images on the display 112 and selecting one of them as the closest to end systole and one of them as the closest to end diastole using the user input device 114. This selection may be made by the user on the basis of an assessment and comparison of the volume of the LV in each of the images as judged by eye, or by noting the points of opening and closing of the mitral valve, or using the QRS complex on an ECG plot, or by any combination of these. This is reasonably easy for a practiced clinician to do. Alternatively the processor 108 may be arranged to use image processing techniques to identify, and measure the volume of, the LV in each of the images, compare the volumes of the LV in the different images, and identify the image with the smallest LV volume as the end systole image and the image with the largest LV volume as the end diastole image. In either case, once the end systole and end diastole images have been identified, they may be identified in the memory 110, for example being marked with an appropriate flag, so that they can be selected and viewed by a user.

Figure 4:
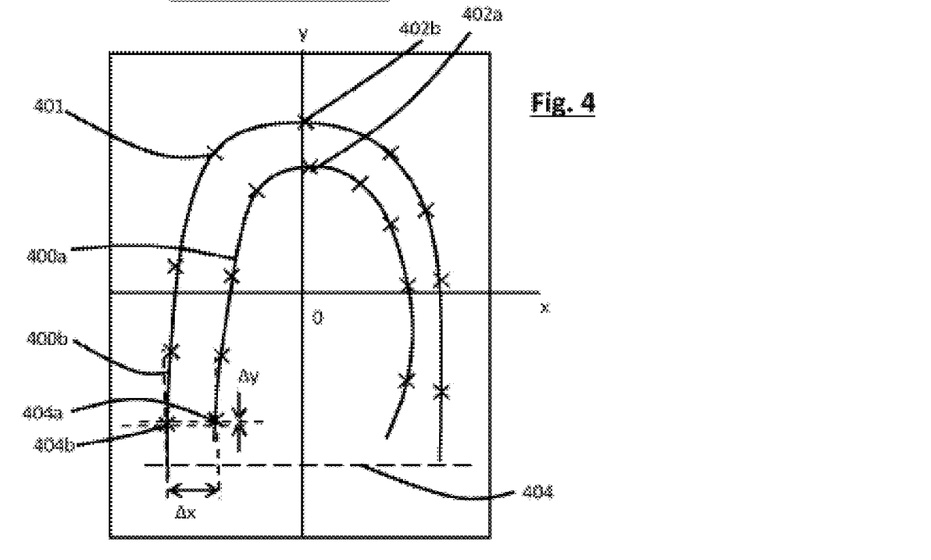
FIG. 4 is a schematic view of a comparison of two images performed by the system of FIG. 1.

Referring to FIG. 4, once the end systole and end diastole images have been identified, corresponding points 401 on the wall of the LV at end systole 400a and at end diastole 400b may be identified at step 304. A Cartesian coordinate system may also be defined, for example having a vertical axis (referred to as the y axis herein) through the apex 402 of the LV and extending along its longitudinal axis, and a horizontal axis (referred to as the x axis herein) through the mid-point of the LV half way between its apex 402 and its base 404. The apex 402 and the base 404 may be identified by the user via the user input, or by image processing. The coordinate of each of the points 400a, 400b on the coordinate system may then be determined and recorded. Since the scale of the image is known from the echocardiography system, the coordinates of each of the points define the position of the point in the plane of the image, and therefore the distance between the two points in each pair indicates the distance moved by the relevant part of the heart between end systole and end diastole. Again, the identification of the points may be done manually by a user selecting each of the points on each of the images using the user input 114, or it may be done by image processing software running on the system 100 and arranged to analyse the shapes of the LV in each of the end systole and end diastole images and identify specific points. These may include for each of the two images, for example, a point at the apex 402*a*, 402*b* of the LV at both end systole and end diastole, a point 404*a*, 406*a*, at one side of the base of the LV, and a point at the other side of the base of the LV, two points at the midpoint of the LV, two points at the start of the apex, and various intermediate points spaced between. Some of these points are described in more detail below with reference to FIGS. 5*a* and 5*b*.

Figure 5A:
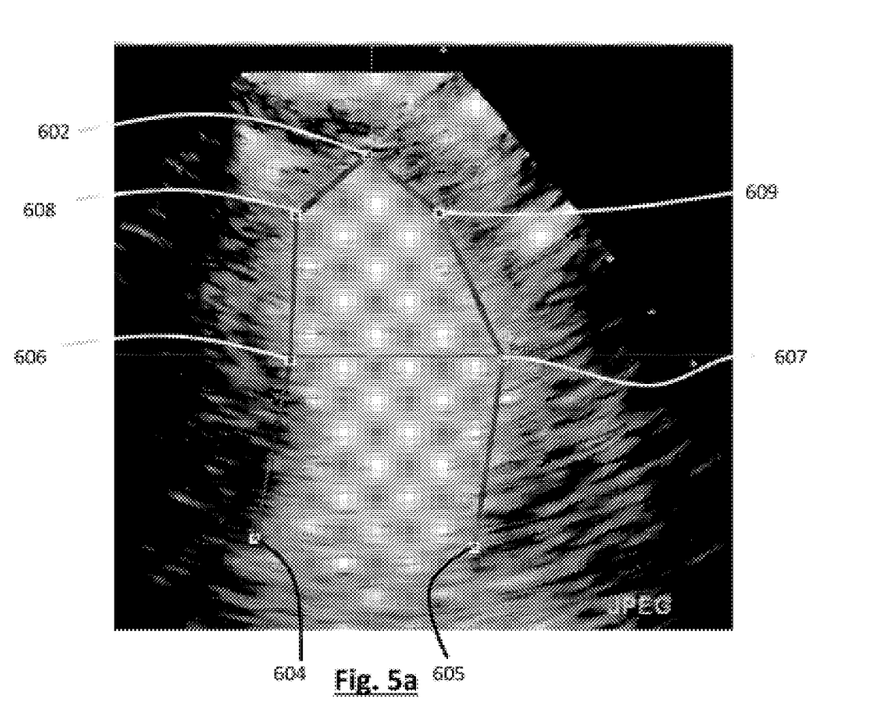
FIGS. 5a and 5b show a sample image at two stages of the analysis as performed by the system of FIG. 1.

Referring to FIG. 5*a*, which shows an echo image acquired with a contrast agent, in each of the images of the LV, the apex 602 of the LV can be located as the extreme end of the LV, and the base of the LV on each side 604, 605 can be located from the shape of the side walls. The y axis can then be defined as the line passing through the apex 602 and the midpoint between the two sides of the base 604, 605. The x axis can then be defined as the line perpendicular to the y axis half way between the apex and the midpoint between the two sides of the base. The mid-point on each side 606, 607 can be identified as the point where the x axis intersects the side wall on that side. The lower end of the apex on each side 608, 609 can also be identified where the sidewalls start to taper towards the apex 602. As mentioned above, each of these points may be identified by a user. Alternatively image processing may be used to identify them. If image processing is used, the outline of the LV is first identified as the boundary between the lighter area within the LV and the darker area of the myocardium forming the walls around it (or vice versa for images acquired without use of a contrast agent). This boundary is not sharp, but algorithms for identifying such boundaries are well known. Once the boundary has been identified, the algorithm may then be arranged to identify the highest point (maximum y value) of the boundary as being the apex 602, and the points where the boundary changes direction at the lower end, for example as can be seen at the point 605 on the right hand side of the base line in FIG. 5*a*. Again algorithms for analysing the radius and direction of curvature, and how that changes around the boundary, can be used to identify these points, and the points 608, 609 at the lower end of the apex.

Figure 5B:
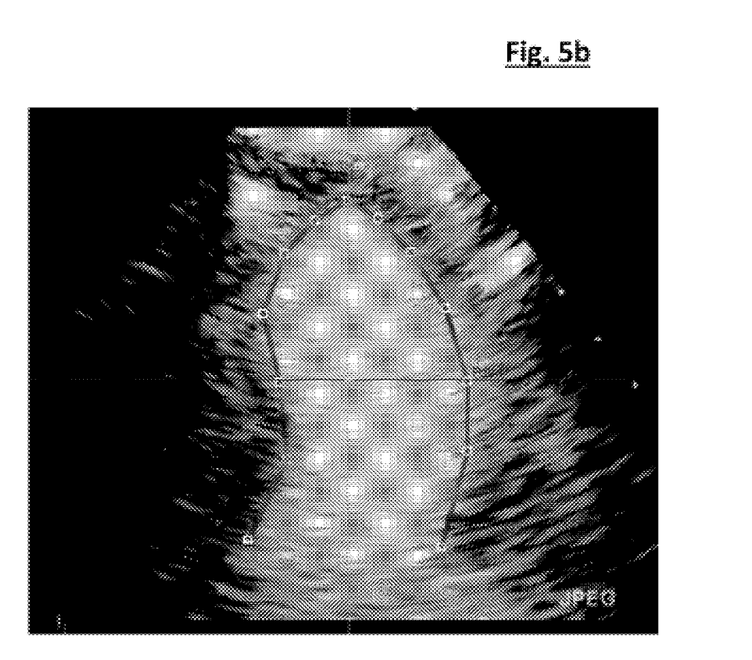
Figure 6A:
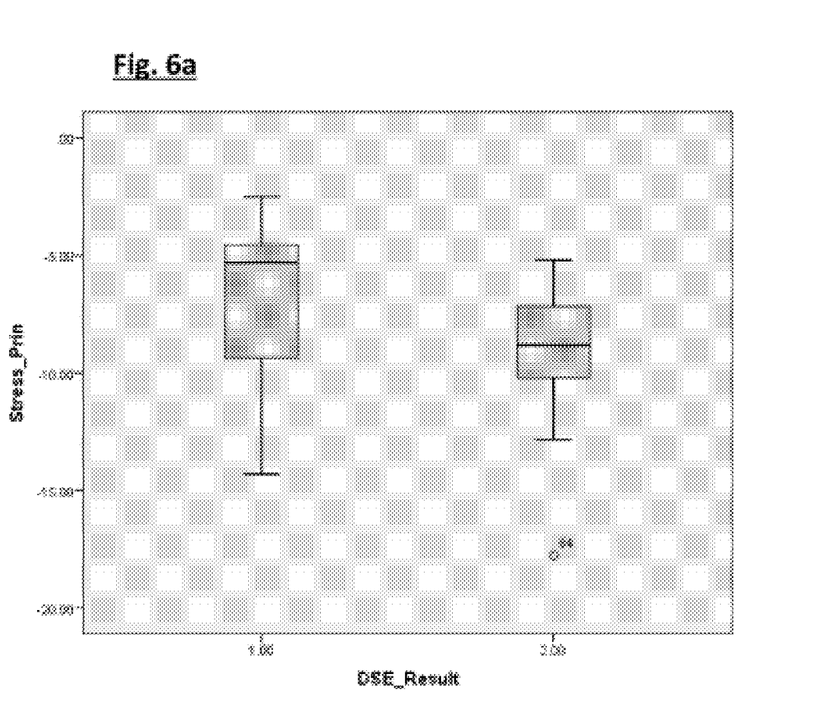
FIGS. 6a and 6b show the results of analysis of sample data obtained using the system of Figure.
Figure 6B:
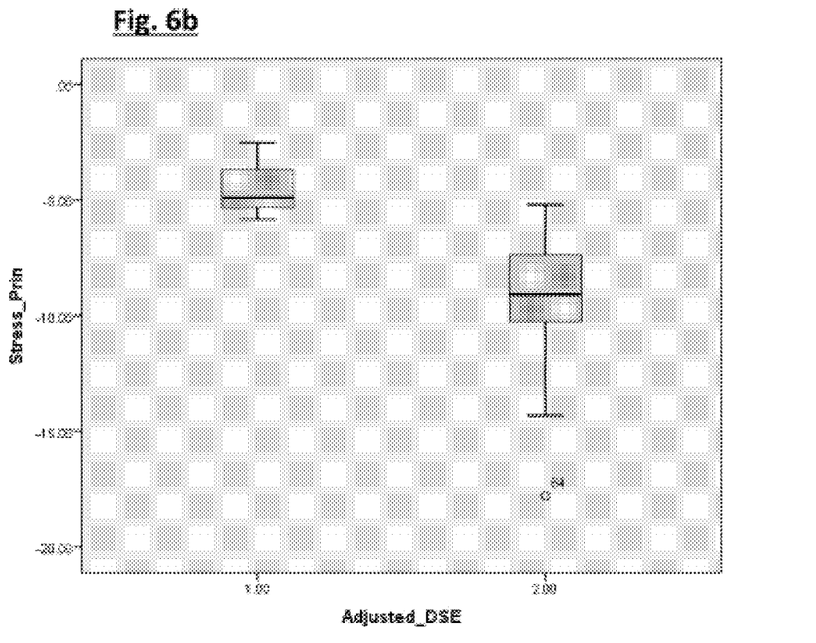

Referring to FIG. 5*b*, further points on the walls of the LV can be identified, either manually or by the processor using simple algorithms. For example these might be points on the side walls equally spaced in the y direction between the points indicated in FIG. 5*a*.

Referring back to FIG. 3, once all of these points have been identified, their x and y coordinates in the Cartesian coordinate system may be stored in the memory 110, for example as an end systole coordinate set including the coordinates of the points on the end systole image and an end diastole coordinate set including the coordinates of the points on the end diastole image. The processor may be arranged at step 306 to calculate, from the two coordinate sets, the transformation in geometry of the LV between end systole and end diastole. For example the processor may be arranged to use the coordinate sets to calculate movement in one or more directions as will now be described in more detail.

Referring back to FIG. 4, the processor 108 is arranged to calculate, for the deformation of the shape of the LV between end systole and end diastole, values for various parameters that quantify the movement of the LV between end systole and end diastole.

The calculation may include working out how far each point has moved in each of the x and y directions, by working out the change in position (End diastole-End systole) along both the x axis and the y axis. This gives a set of x axis movements $\Delta x$, with one value for each corresponding pair of points, as shown in FIG. 4 for the points 404*a*, 404*b*, and a set of y axis movements $\Delta y$, again with one value for each corresponding pair of points. Each of these values may be a simple distance with no indication of direction. The mean change of all the points in both the x axis ($\Delta X$) and y axis ($\Delta Y$) may then be calculated separately so as to provide an average $\Delta x$ value or x direction movement $\Delta X$, and an average $\Delta y$ value or y direction movement $\Delta Y$ for the entire ventricle. If each of the individual movement values are purely distance, without any indication of whether they are in the positive or negative x or y direction, then these averages will describe the total amount of movement, but not give an indication of the direction or of whether different parts of the LV wall are moving in the same direction or opposite directions.

Another parameter that maybe calculated is, for each point on the LV, i.e. each pair of points on the images, to calculate the mean of the x and y direction movements $\Delta x$ and $\Delta y$, where the mean value for each point $\Delta xy=(\Delta x+\Delta y)/2$. The mean of all the values of $\Delta xy$ for all points can then be calculated to a value for the entire ventricle $\Delta XY$. This calculation is similar to the calculation of shear strain and is therefore referred to herein as the shear transformation. It will be appreciated that, for a given distance of movement, this parameter will be largest for movements at 45 degrees to both of the x and y axes, and smallest for movements along one of the axes.

A further parameter that can be calculated is similar to the principal transformation that can be calculated from x and y strain components, and is therefore referred to herein as the principal transformation, given by $$\text{principal transformation}=C1(\Delta X+\Delta Y-\sqrt{(\Delta X+\Delta Y)^2+C2\Delta XY^2})$$

where C1 and C2 are constants. For example C1 may be ½ and C2 may be 4. These values were used in the examples described below.

This transformation is closely related to the shear transformation and therefore tends to vary in a similar way to that parameter, but has a negative value indicating contraction of the heart. However, as indicated by the test results below, the principal transformation value can give a more reliable diagnosis in some cases, in particular of CAD.

It will be appreciated that each of these parameters relates to changes between end systole and end diastole in a single coronary cycle. However in stress echocardiography, (or corresponding tests carried out with other imaging methods) there will be one value for each parameter for the heart at rest and one value for the heart at stress. Comparing those values, for example determining the difference between them, gives further information about heart function that can be used in diagnosis.

Once the x and y movements, and shear and principal transformation values have been calculated, the processor is then arranged at step 308 to compare these with reference values stored in the memory 110 to make a diagnosis of one or more specific heart conditions, and to generate a diagnostic output. The output may be a simple binary output indicating a positive or negative diagnosis. The processor unit 106 may be arranged to display the output on the display 112. Alternatively, or in addition, it may be arranged to store the output as data in association with the images on which it was based, for example by adding output data, indicative of the diagnosis, to a file in which the images are stored.

The reference values may for example be determined by analysis of images of hearts some of which do and some of which do not have the specific heart conditions to determine for example threshold values which are indicative of a specific condition.

The reference values can be determined by means of a learning algorithm which, for example, can be run on the processor unit 106, and which uses a database of stress echo images with associated diagnoses as determined by conventional methods, which may be stored in the memory 110. Specifically the database may include a large number of sets of images, each set comprising an end systole image and an end diastole image for both rest condition and stress condition, together with, for each set of images, an associated diagnosis, such as a positive or negative diagnosis for CAD. The learning algorithm may be arranged to analyse the images to calculate values of the various parameters described above, and then to determine the correlation between the diagnosis and the values of each of the various parameters.

Analysis was carried out on sample images from 70 subjects. All results generated were from an apical 4 chamber view. Firstly the values were compared for positive and negative outcomes as determined from the DSE results. Then the comparison was repeated with the DSE results corrected for confirmed false positives in the DSE results. Table 1 Shows values of the principal transformation (in mm), shear transformation value (in mm), and mean ΔX (in mm) at rest and stress for DSE outcome (1=Pos, 2=Neg) in the Apical 4 Chamber view.

-continued

| Group Statistics | | | | | |
|---|---|---|---|---|---|
| | DSE_Result | N | Mean | Std. Deviation | Std. Error Mean |
| Rest_Prin | 1.00 | 9 | −7.7332 | 3.86497 | 1.28832 |
| | 2.00 | 61 | −9.3163 | 2.41589 | .30932 |
| Rest_Shr | 1.00 | 9 | 17.7267 | 9.16943 | 3.05648 |
| | 2.00 | 61 | 21.5356 | 5.50610 | .70498 |
| Stress_Shr | 1.00 | 9 | 17.0074 | 8.06969 | 2.68990 |
| | 2.00 | 61 | 22.2608 | 4.56871 | .58496 |
| Rest_X | 1.00 | 9 | 18.8694 | 11.02116 | 3.67372 |
| | 2.00 | 61 | 21.8492 | 6.65078 | .85155 |
| Stress_X | 1.00 | 9 | 19.9334 | 9.80639 | 3.26880 |
| | 2.00 | 61 | 25.8710 | 7.43965 | .95255 |

Table 2 Shows means of Principal transformation value (in mm), Shear transformation (in mm) and X transformation (in mm) at rest and stress for Adjusted DSE outcome (1=Pos, 2=Neg).

| Group Statistics | | | | | |
|---|---|---|---|---|---|
| | Adjusted_DSE | N | Mean | Std. Deviation | Std. Error Mean |
| Stress_Prin | 1.00 | 7 | −4.4716 | 1.29120 | .48803 |
| | 2.00 | 63 | −9.1203 | 2.24588 | .28295 |
| Rest_Prin | 1.00 | 7 | −5.3352 | 1.21275 | .45838 |
| | 2.00 | 63 | −9.5325 | 2.44136 | .30758 |
| Rest_Shr | 1.00 | 7 | 12.0645 | 2.74525 | 1.03761 |
| | 2.00 | 63 | 22.0438 | 5.58342 | .70344 |
| Stress_Shr | 1.00 | 7 | 12.2348 | 3.81629 | 1.44242 |
| | 2.00 | 63 | 22.6243 | 4.44025 | .55942 |
| Rest_X | 1.00 | 7 | 11.6937 | 2.73459 | 1.03358 |
| | 2.00 | 63 | 22.5519 | 6.84823 | .86280 |
| Stress_X | 1.00 | 7 | 14.1727 | 4.81157 | 1.81860 |
| | 2.00 | 63 | 26.3226 | 7.29318 | .91885 |

Table 3 Shows Independent samples T-Test for variables vs adjusted DSE.

| Independent Samples Test | | | | | | |
|---|---|---|---|---|---|---|
| | | Levene's Test for Equality of Variances | | | | |
| | | F | Sig. | t | df | Sig. (2-tailed) |
| Stress_Prin | Equal variances assumed | 1.705 | .196 | 5.356 | 68 | .000 |
| | Equal variances not assumed | | | 8.240 | 10.596 | .000 |
| Rest_Prin | Equal variances assumed | 2.355 | .130 | 4.466 | 68 | .000 |
| | Equal variances not assumed | | | 7.804 | 12.377 | .000 |
| Rest_Shr | Equal variances assumed | 2.106 | .151 | −4.644 | 68 | .000 |
| | Equal variances not assumed | | | −7.961 | 12.527 | .000 |
| Stress_Shr | Equal variances assumed | .194 | .661 | −5.942 | 68 | .000 |
| | Equal variances not assumed | | | −6.715 | 7.923 | .000 |
| Rest_X | Equal variances assumed | 5.696 | .020 | −4.136 | 68 | .000 |
| | Equal variances not assumed | | | −8.065 | 16.500 | .000 |
| Stress_X | Equal variances assumed | .927 | .339 | −4.290 | 68 | .000 |
| | Equal variances not assumed | | | −5.963 | 9.395 | .000 |

| Group Statistics | | | | | |
|---|---|---|---|---|---|
| | DSE_Result | N | Mean | Std. Deviation | Std. Error Mean |
| Stress_Prin | 1.00 | 9 | −6.8214 | 4.08788 | 1.36263 |
| | 2.00 | 61 | −8.9260 | 2.20018 | .28170 |

Machine Learning Results

From the values of the various parameters obtained from the sample data, machine learning may be used to determine the accuracy of each parameter as an indicator of adjusted DSE outcome. Using the data above, a J48 pruned decision tree with 10 fold cross validation method was used to classify the data. The accuracy of each parameter as an indicator of diagnostic outcome is summarized in the tables below, in which the following abbreviations used are:
TP=true positive
FP=false positive
FN=false negative
TN=true negative
PPV=positive predictive value
NPV=negative predictive value

TABLE 4

Accuracy of Consultant Interpretation

| J48 | TP = 6 | FN = 1 |
|---|---|---|
| Accuracy = 94.3% | FP = 3 | TN = 60 |
| Sensitivity = 85.7% | PPV = 66.7% | |
| Specificity = 95% | NPV = 98.4% | |

TABLE 5

Accuracy of Stress Principal Transformation for Adjusted DSE outcome

| J48 Value = −5.95 | TP = 7 | FN = 0 |
|---|---|---|
| Accuracy = 95.7% | FP = 3 | TN = 60 |
| Sensitivity = 100% | PPV = 70% | |
| Specificity = 95.2% | NPV = 100% | |

TABLE 6

Accuracy of Rest Principal Transformation for Adjusted DSE outcome

| J48 Value = −6.92 | TP = 5 | FN = 2 |
|---|---|---|
| Accuracy = 88.6% | FP = 6 | TN = 57 |
| Sensitivity = 71.4 | PPV = 45.5% | |
| Specificity = 90.5% | NPV = 96.6% | |

TABLE 7

Accuracy of Stress Shear Transformation for Adjusted DSE outcome

| J48 Value = 15.85 | TP = 6 | FN = 1 |
|---|---|---|
| Accuracy = 95.7% | FP = 2 | TN = 61 |
| Sensitivity = 85.7% | PPV = 85.7 | |
| Specificity = 96.8% | NPV = 98.4 | |

TABLE 8

Accuracy of Rest Shear Transformation for Adjusted DSE Outcome

| J48 Value = 15.35 | TP = 5 | FN = 2 |
|---|---|---|
| Accuracy = 91.4% | FP = 4 | TN = 59 |
| Sensitivity = 71.4 | PPV = 55.6% | |
| Specificity = 93.7% | NPV = 96.7% | |

Figure 7:
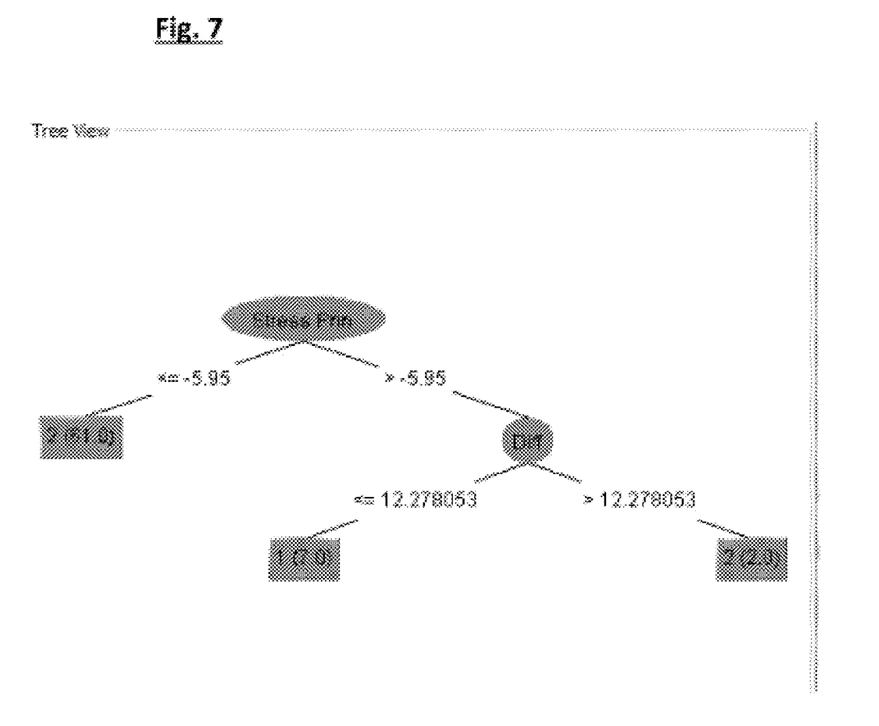
FIG. 7 is a flow diagram showing the algorithm used to produce the results of FIGS. 6a and 6b.

Then from all of the variables, using machine learning, a decision tree which is shown in FIG. 7 was derived to provide accurate diagnosis from the data. The decision tree defines a series of decision points, each of which defines a reference or threshold value of a parameter. The decision tree outlines a simple algorithm which operates as follows. Firstly the principal transformation of the LV as described above is determined for the stress condition of the heart. If the transformation is less than −5.95 mm (i.e. a negative value with magnitude greater than 5.95 mm) then the diagnosis is negative. If the value is greater than −5.95 mm then difference in principal transformation between rest and stress conditions is greater than 12.278053 mm then the diagnosis is negative, but if it is less than that distance, the diagnosis is positive. It will be appreciated that the structure of the decision tree, and the reference or threshold values at each decision point in the decision tree, will depend on the diagnosis that is to be made.

The decision tree was then used on the sample data to test its accuracy and the outcome is given below.

Machine Learning on all Variables

TABLE 9

Accuracy of J48 decision tree for Adjusted DSE Outcome

| J48 Value = FIG. 1 Algorithm | TP = 5 | FN = 2 |
|---|---|---|
| Accuracy = 100% | FP = 4 | TN = 59 |
| Sensitivity = 100% | PPV = 100% | |
| Specificity = 100% | NPV = 100% | |

To test whether a 2 chamber view could be used instead of a 4 chamber view in a similar diagnostic system, two chamber views corresponding to each of the four chamber views in the sample data were analysed in the same way to derive the same parameters of principal transformation, shear transformation, and radial (X) and longitudinal (Y) movements.

TABLE 10

Intraclass correlation coefficient of translation measurement parameters between 4 chamber and 2 chamber views.

| Prin transformation | 0.84 |
|---|---|
| Radial displacement (ΔX) | −0.23 |
| Shear transformation | 0.36 |
| Longitudinal displacement (ΔY) | −0.532 |

A very significant result is the similarity in principal transformation values between the 4 and 2 chamber view. This implies that not only is the principal vector a sensitive parameter for detecting disease, it also implies that it gives a 3D functional assessment from a 2D view

TABLE 11

Principal transformation value stats for other Disease Cohorts

| | Principal transformation 2ch | Principal transformation 4ch |
|---|---|---|
| HCM | −4.5 | −3.6 |
| Mitral Regurgitation | −6.0 | −6.1 |
| Healthy | −7.7 | −7.5 |

Table 11 illustrates that the principal transformation is reduced in other disease cohorts (hypertrophic cardiomyopathy (HCM) and mitral regurgitation) implying it is also sensitive at detecting hypertrophy, cardiomyopathies and valve disorders. Notice that the principal vector was reduced in both the 4 chamber and the 2 chamber views indicating that it is sensitive at detecting abnormalities in the heart from just a single plane. Specifically with regard to HCM where the hypertrophy occurred only in the 4 chamber view yet the principal transformation was still significantly reduced in the 2 chamber view.

It will be appreciated that analysis of images in just one plane can be used to diagnose a range of diseases, and that various different parameters can be used to develop a decision tree which provides more accurate diagnosis than a single parameter.

The invention claimed is:

1. A system for diagnosing a heart condition comprising:
an imaging system arranged to acquire two images of the heart at respective points in a cardiac cycle;
locating means for locating positions of a series of pairs of points on the images, each pair of points indicating respective positions of a single part of the heart in the two images; and
processing means arranged to calculate from the positions of said pairs of points a value of at least one parameter of a deformation of the heart, and to compare the value of the at least one parameter with reference data to generate a diagnostic output, wherein the at least one parameter includes a sum of displacements in longitudinal and radial directions for at least one of said pairs of points.

2. A system according to claim 1 wherein the at least one parameter includes a displacement in at least one direction.

3. A system according to claim 2 wherein the displacement is a mean of the displacements for all of said parts of the heart in at least one direction.

4. A system according to claim 1 wherein the locating means comprises a user input device arranged to enable a user to locate said pairs of points and to record the positions of said pairs of points.

5. A system according to claim 1 wherein the imaging system is arranged to store the images as respective image data sets; and
the locating means is arranged to process the image data sets to determine the locations of said pairs of points and to record the positions of said pairs of points.

6. A system according to claim 1 wherein the at least one parameter comprises a plurality of parameters and the processing means is arranged to compare the value of each of the plurality of parameters with a respective reference value.

7. A system according to claim 6 wherein the processing means is arranged to use machine learning to define a decision tree for generating the diagnostic output from the values of the plurality of parameters.

8. A method of producing a system according to claim 1, the method comprising:
analyzing a set of images, wherein each of the images has a diagnostic outcome associated with a corresponding image;
calculating a value of the at least one parameter for each of the images;
analyzing the values and the diagnostic outcomes corresponding to the images to determine a relationship or correlation between the value and the diagnostic outcome; and
using machine learning to develop a decision tree for generating the diagnostic output from the values of the plurality of parameters.

9. A system for measuring deformation of a heart, the system comprising:
an imaging system arranged to acquire two images of the heart at respective points in a cardiac cycle;
locating means for locating positions of a series of pairs of points on the images, each pair of points indicating respective positions of a single part of the heart in the two images; and
processing means arranged to calculate from the positions of said pairs of points a value of at least one parameter of the deformation of the heart, wherein the at least one parameter includes the sum of displacements in the longitudinal and radial directions for at least one of said pairs of points.

10. A system according to claim 9 wherein the at least one parameter includes a displacement in at least one direction.

11. A method of measuring deformation of a heart, the method comprising:
acquiring two images of the heart at respective points in a cardiac cycle;
locating positions of a series of pairs of points on the two images, each pair of points indicating respective positions of a single part of the heart in the two images;
calculating from the positions of said pairs of points a value of at least one parameter of the deformation of the heart, wherein the at least one parameter includes the sum of displacements in longitudinal and radial directions for at least one of said pairs of points; and
comparing the value of the at least one parameter with reference data to generate a diagnostic output.

12. A method according to claim 11 wherein the at least one parameter includes a displacement in at least one direction.

13. A method according to claim 12 wherein the displacement is a mean of the displacements for all of said parts of the heart in at least one direction.

14. A method according to claim 11 further comprising processing image data sets to determine respective locations of said pairs of points and recording the positions of said pairs of points.

15. A method according to claim 11 wherein the at least one parameter comprises a plurality of parameters and comparing the value of the at least one parameter with the reference data includes comparing a value of each of the parameters with a respective reference value.

16. A method according to claim 11 further comprising using machine learning to define a decision tree for generating the diagnostic output from the values of the parameters.

17. A system according to claim 1 wherein the at least one parameter comprises principal transformation.

18. A system according to claim 1 wherein the at least one parameter comprises shear transformation.

19. A method according to claim 11 wherein at least one parameter comprises a principal transformation.

20. A method according to claim 11 wherein the at least one parameter comprises a shear transformation.

* * * * *